(12) United States Patent
Siegel et al.

(10) Patent No.: US 8,173,844 B2
(45) Date of Patent: *May 8, 2012

(54) METHOD FOR PRODUCING O-ALKYLATED CYCLIC AMINOALCOHOLS

(75) Inventors: Wolfgang Siegel, Limburgerhof (DE); Gerd Haderlein, Grünstadt (DE); Tobias Stab, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/158,402

(22) PCT Filed: Dec. 11, 2006

(86) PCT No.: PCT/EP2006/069529
§ 371 (c)(1),
(2), (4) Date: Jun. 20, 2008

(87) PCT Pub. No.: WO2007/074047
PCT Pub. Date: Jul. 5, 2007

(65) Prior Publication Data
US 2008/0306304 A1 Dec. 11, 2008

(30) Foreign Application Priority Data
Dec. 22, 2005 (EP) .................................... 05112824

(51) Int. Cl.
C07C 211/00 (2006.01)
(52) U.S. Cl. ...................................................... 564/453
(58) Field of Classification Search .................. None
See application file for complete search history.

(56) References Cited

U.S. PATENT DOCUMENTS

| 6,133,319 A * | 10/2000 | Widdowson | 514/598 |
| 6,451,804 B1 * | 9/2002 | Dunn et al. | 514/262.1 |
| 2004/0152600 A1 * | 8/2004 | Dahlmann et al. | 507/100 |
| 2005/0187220 A1 | 8/2005 | Sundermann et al. | |

FOREIGN PATENT DOCUMENTS

| DE | 1034447 | 7/1958 |
| WO | WO-2005095377 | 10/2005 |
| WO | WO-2006050076 | 5/2006 |

OTHER PUBLICATIONS

Khabnadideh et al. Bioorganic and Medicinal Chemistry Letters 13 (2003) 2863-2865.*
U.S. Appl. No. 12/158,517, filed Jun. 2008, Siegel, Wolfgang.*
Nishi et al., "Studies on 2-Oxoquinoline Derivatives as Blood Platelet Aggregation Inhibitors. IV. Synthesis and Biological Activity of the Metabolites of 6-[4-(1-Cyclohexyl-1H-5-tetrazolyl)butoxy]-2-oxo-1,2,3,4-tetrandroquinoline (OPC-13013)", Chem. Pharm. Bull., vol. 33, No. 3, pp. 1140-1147, 1985.
Arndt et al., "Folding Propensity of Cyclohexylether-δ-peptides", American Chemical Society, vol. 6, No. 19, pp. 3269-3272, 2004.
Lewis et al., "Enzyme inhibition during the conversion of squalene to cholesterol", Elsevier Science Inc: Steorids, vol. 60, pp. 475-483, 1995.
Kikelj et al., "N-{trans-2-[[2'-(Acetylamino) cyclohexyl] acetyl}-L-alanyl-D-glutamic Acid: A Novel Immunologically Active Carbocyclic Muramyl Dipeptide Analogue", Journal of Medical Chemistry, vol. 41, No. 4, pp. 530-539, 1998.
Arndt et al., "Cyclohexylether δ-Amino Acids: New Leads for Selectively Filters in Ion Channels", Angew. Chem. Int. Ed., vol. 40, No. 11, pp. 2076-2078, 2001.
Laleu et al., "Bent Structure and Dynamic Stereochemistry of Chiral Acridinium Cations", Journal of Organic Chemistry, vol. 68, No. 16, pp. 6304-6308, 2003.
Price et al., "A novel synthetic approach towards 2-guanidinomethyl-4(5)-sulfamoylimidazoles", Tetrahedron Letters 45, pp. 5581-5583, 2004.
Whitesell et al., "Asymmetric Induction. Enantioselective Alkylation of Cyclohexanone", Journal of Organic Chemistry, vol. 42, No. 2, pp. 377-378, 1977.
Surrey et al., "New Amoebacides-VI.[1] The Preparation of some N,N'-Disubstituted-N,N'-bis(haloacyl)-1,4-xylylenediamines", Journal of Medicinal and Pharmaceutical Chemistry, vol. 3, No. 3, pp. 409-417, 1961.
Meyers et al., Asymmetric Synthesis of (+)- or (−)-2-Methyloctanal via the Metalloenamines of Chrial Alkoxy Amines:, Journal of Organic Chemistry, vol. 43, No. 5, pp. 892-898, 1978.
Hu et al., "Selective O-Benzylation of Arninoalkanols", Synthetic Communications, vol. 25, No. 6, pp. 907-913, 1995.

* cited by examiner

Primary Examiner — Daniel Sullivan
Assistant Examiner — Clinton Brooks
(74) Attorney, Agent, or Firm — Connolly Bove Lodge & Hutz LLP

(57) ABSTRACT

A process for preparing O-alkylated amino alcohols of the formula (I) by reacting N-unsubstituted or N-monosubstituted amino alkoxide salts with alkyl halides, the amino alkoxide salts being formed by means of alkoxides

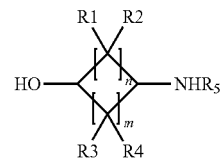

2 Claims, No Drawings

METHOD FOR PRODUCING O-ALKYLATED CYCLIC AMINOALCOHOLS

CROSS REFERENCE TO RELATED APPLICATIONS

This application is a National Phase filing under 35 U.S.C. §371 of PCT/EP2006/069529 filed Dec. 11, 2005, which claims priority to Patent Application No. 05112824.7, filed in Europe on Dec. 22, 2005. The entire contents of each of the above-applications are incorporated herein by reference.

STATE OF THE ART

The present invention is directed to a process for preparing cyclic N-unsubstituted and N-monosubstituted amino alkyl ethers or amino benzyl ethers. In particular, the invention is concerned with the regioselective O-alkylation or O-benzylation of cyclic N-unsubstituted and N-monosubstituted amino alcohols. Such amino alkyl ethers and amino benzyl ethers are valuable intermediates for the preparation of bioactive ingredients (T. Nishi et al. Chem. Pharm. Bull. 1985, 33(3), 1140-1147; D. Lewis et al. Steroids, 1995, 60, 475-483; D. Kikelj et al. J. Med. Chem. 1998, 41, 530-539; Koert et al. Ang. Chem. Int. Ed. 2001, 40(11), 2076-2078) and chiral auxiliaries for chemical synthesis (J. Lacour et al. J. Org. Chem. 2003, 68(16), Price et al. Tetrahedron Letters 2004, 45, 5581-5583).

Ether formations are one of the standard reactions of organic chemistry which are also carried out on the industrial scale (Organikum, VEB, Berlin 1986, p. 191ff.).

In principle, a distinction is drawn between the acidic and the basic Williamson ether synthesis. In the Williamson O-alkylation, an alkoxide anion is obtained and is reacted with a compound having a nucleofugic leaving group, for example an alkyl halide.

Compounds with a nucleofugic leaving group—i.e. electrophilic reagents—for example alkyl halides, alkyl sulfates, alkylsulfonates, but also benzyl halides or the like, also react, however, readily with nucleophilic amino functions of an organic molecule. When the intention is now to basically etherify an alcohol which also comprises an unprotected or only monosubstituted amino function in the molecule, conditions have to be found under which the reaction of the amino function as far as possible does not occur and the alcohol function is converted fully. Such syntheses are described in the literature differently and with varying success. They are usually the reaction of the amino alcohol with extremely strong bases which react irreversibly to initially form the alkali metal alkoxide ion, which is followed by the reaction with the electrophile (Whitesell et al. J. Org. Chem. 1977, 42, 377; Mayer et al. J. Med. Pharm. Chem. 1961, 3, 409; Meyers et al. J. Org. Chem. 1978, 43, 892, Hu et al. Synth. Commun. 1995, 25(6), 907.). In the case of the use of alkali metal hydrides, the dangerous evolution of hydrogen additionally has to be brought under control on the production scale.

DE 103 44 447 A1 describes the use of alkali metal alkoxides as a deprotonating reagent, although only acyclic amino alcohols are reacted, which can be used advantageously can be used on the industrial scale in particular.

OBJECTIVE

It was therefore an object of the present invention to specify a further process for regioselective O-alkylation and O-benzylation of N-unprotected and N-monosubstituted cyclic amino alcohols, which, in contrast to the prior art, can also be employed advantageously on the industrial scale and for cyclic substrates. In particular, the process should be superior to the prior art processes from the economic and ecological standpoint, and help to permit the generation of the ethers desired in improved yields and regioselectivities, even for the cyclic amino alcohols which have a very different reactivity from acyclic amino alcohols.

SUBJECT-MATTER OF THE INVENTION

The invention provides a process for preparing O-alkylated amino alcohols of the formula (I) by reacting N-unsubstituted or N-monosubstituted amino alkoxide salts with alkyl halides, the amino alkoxide salts being formed by means of alkoxides.

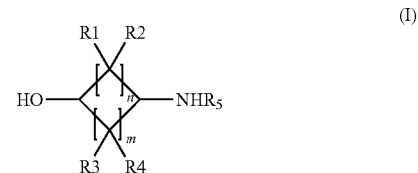

where
each independently, n=0, 1, 2, 3, 4 and m=0, 1, 2, 3, 4, and R1, R2, R3, R4 and R5 are each independently H, substituted and unsubstituted $(C_1-C_8)$-alkyl, $(C_3-C_8)$-cycloalkyl, $(C_1-C_8)$-alkyl-$(C_3-C_8)$-cycloalkyl, $(C_3-C_8)$-cycloalkyl-$((C_1-C_8)$-alkyl)1-3, $(C_2-C_8)$-alkenyl, $(C_2-C_8)$-alkynyl, $(C_6-C_{18})$-aryl, $(C_7-C_{19})$-aralkyl radical, $(C_6-C_{18})$-aryl-$((C_1-C_8)$-alkyl) 1-3, $(C_3-C_{18})$-heteroaryl radical, $(C_4-C_{19})$-heteroaralkyl, $(C_3-C_{18})$-heteroaryl radical $((C_1-C_8)$-alkyl)1-3.

$(C_1-C_8)$-Alkyl is considered to be: methyl, ethyl, n-propyl, isopropyl, n-butyl, isobutyl, sec-butyl, tert-butyl, pentyl, hexyl, heptyl or octyl including all bonding isomers.

With the exception of methyl, $(C_2-C_8)$-alkenyl is understood to mean a $(C_1-C_8)$-alkyl radical as described above which has at least one double bond.

With the exception of methyl, $(C_2-C_8)$-alkynyl is understood to mean a $(C_1-C_8)$-alkyl radical as described above which has at least one triple bond.

$(C_3-C_8)$-Cycloalkyl is understood to mean cyclopropyl, cyclobutyl, cyclopentyl, cyclohexyl or cycloheptyl radicals, etc. These may have N-, O-containing radicals in the ring, for example 1-, 2-, 3-, 4-piperidyl, 1-, 2-, 3-pyrrolidinyl, 2-, 3-tetrahydrofuryl, 2-, 3-, 4-morpholinyl.

A $(C_6-C_{18})$-aryl radical is understood to mean an aromatic radical having from 6 to 18 carbon atoms. In particular, these include compounds such as phenyl, naphthyl, anthryl, phenanthryl, biphenyl radicals.

A $(C_7-C_{19})$-aralkyl radical is a $(C_6-C_{18})$-aryl radical bonded to the molecule via a $(C_1-C_8)$-alkyl radical.

In the context of the invention, a $(C_3-C_{18})$-heteroaryl radical denotes a five-, six- or seven-membered aromatic ring system composed of from 3 to 18 carbon atoms, which has heteroatoms, for example nitrogen, oxygen or sulfur, in the ring. Such heteroaromatics are considered in particular to be radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. A $(C_4-C_{19})$-heteroaralkyl is understood to mean a heteroaromatic system corresponding to the $(C_7-C_{19})$-aralkyl radical.

The above-defined radicals may be either unsubstituted or mono- or polysubstituted by radicals which either behave inertly under the reaction conditions or which have been masked beforehand by protecting groups. Examples of substituents are OH; $NH_2$, SH, $NO_2$, CN, CO, COOH, F, Cl, Br, I.

In the context of the invention, the term enantiomerically enriched is understood to mean the proportion of one enantiomer in a mixture with its optical antipode in a region of >50% and <100%.

The N-unsubstituted and N-monosubstituted amino alcohols used may be achiral or chiral. They may also be present as racemic, enantiomerically enriched or diastereomerically enriched mixtures. Preference is given to the use of N-unsubstituted or N-monosubstituted 2-aminocycloalkanols or, more preferably, of N-unsubstituted or N-monosubstituted trans-2-aminocycloalkanols. These are obtainable, for example, by ring-opening the corresponding epoxides with ammonia or monosubstituted amines.

Very particular preference is given to the use of N-unsubstituted or N-monosubstituted trans-2-aminocyclopentanol or N-unsubstituted or N-monosubstituted trans-2-amino-cyclohexanol.

The alkyl halides employed may be all compounds known to those skilled in the art for this reaction. Preference is given to using (C1-C8)-alkyl chlorides or bromides in the inventive reaction. Very particular preference is given here to primary and secondary alkyl halides, of which those having methyl or ethyl radicals are particularly recommended. Particular preference is given to alkyl chlorides. In addition to the alkyl halides, it is also possible to use alkyl sulfates as alkylating reagents.

The benzyl halides used may preferably be benzyl chloride or benzyl bromide, and the compounds may be mono- or polysubstituted on the aryl radical by common substituents. Particular preference is given to benzyl chloride.

The dependent claims relate to preferred embodiments of the process according to the invention.

It is advantageous for the reaction that it is carried out in a solvent. With regard to the selection of the solvent, the person skilled in the art is guided by the product yield, reaction rate, handling of the alkoxide suspensions and the cost of the solvent. Advantageous solvents are those which can be mixed with the amino alcohol, are chemically inert, i.e. do not react with the amino alcohol, an alkoxide or the alkylating or benzylating agent, and typically have a boiling point which is above that of the alcohol which is formed from the corresponding alkoxide in the deprotonation of the amino alcohol. Typical solvents are aliphatics or aromatics having appropriate boiling points, including mixtures and boiling fractions.

Preference is given to aromatics such as toluene, ortho-xylene, meta-xylene, para-xylene, ethylbenzene, methylethylbenzene, other alkylbenzenes, etc., pp. or mixtures thereof. Particular preference is given to xylene isomer mixtures, since, especially in the case of the cyclic amino alcohols used, the amino alkoxide salts precipitated and formed are obtained in a form which can be handled particularly readily and can be freed of residual alcohol easily. In addition, simple recycling of the solvent streams is possible.

The N-unsubstituted and N-monosubstituted amino alkoxide salts to be converted are generated by means of alkali metal alkoxides. The alkali metal alkoxides may be used in the reaction as a solid or preferably dissolved or suspended in volatile solvents. In this case, the reaction can be completed by distilling off the alcohol which forms and the solvent used if appropriate. In order to avoid the use of different solvents, whose mixtures would have to be separated again from one another by distillation in a laborious manner in the recycling, particular preference is given to using the alkali metal alkoxides as a solution in the corresponding alcohol for the deprotonation.

As outlined above, the alcohol which forms in the inventive reaction can be removed by distillation from the reaction mixture. It is therefore advantageous that alkali metal salts of short-chain alcohols are used for the deprotonation, since they have a comparatively low boiling point and are thus easy to remove. The alkali metal alkoxide/alcohol mixture used in the reaction by the person skilled in the art is preferably sodium methoxide or potassium methoxide in methanol or sodium ethoxide or potassium ethoxide in ethanol. Particular preference is given to using sodium methoxide in methanol.

After the reaction has ended, the mixture can, if appropriate, be allowed to cool and the precipitated inorganic salt can be filtered off or removed in another manner known to those skilled in the art, for example with a centrifuge, cyclotron etc. Alternatively, the inorganic salt formed can also remain in the crude mixture. Thereafter, the product is isolated in a manner known to those skilled in the art, preferably by distillation. The distillation can advantageously be effected by a single-stage evaporation, preferably by fractional distillation in one or more, such as 2 or 3, distillation apparatuses. Useful apparatus for the distillation is apparatus customary for this purpose, as described, for example, in: Kirk-Othmer, Encyclopedia of Chemical Technology, 3rd ed., Vol. 7, John Wiley & Sons, New York, 1979, page 870-881, such as sieve tray columns, bubble-cap tray columns, columns with structured packings, columns with random packings, columns with side draw or dividing wall columns. The distillation can be carried out in batch mode or continuously. Owing to the thermal sensitivity of the substrates, the distillation is preferably carried out at reduced pressure—depending on the corresponding reaction product—of from 1 to 500 hPa, preferably from 5 to 200 hPa. [0018] (C1-C8)-alkyl is considered to be methyl, ethyl, n-propyl, isopropyl, n-butyl, isobutyl, sec-butyl, tert-butyl, pentyl, hexyl, heptyl or octyl including all bonding isomers.

The N-unsubstituted and N-monosubstituted amino alkoxide salts to be converted are generated by means of tertiary-alkali metal alkoxides. The tertiary alkali metal alkoxides can be used in the reaction preferably as a solid or else dissolved or suspended in volatile solvents. In this case, the amino alcohol and the tertiary alkoxide can be initially charged together and heated; it is no longer necessary to distill off the alcohol formed. To this end, tertiary sodium alkali metal alkoxides or potassium alkali metal alkoxides, preferably C4-C10 alkoxides, more preferably potassium tert-butoxide, are used for the deprotonation. The advantage of the tertiary alkoxides is that they are more basic than the amino alcohols used, and deprotonation of the amino alcohols is thus ensured. Secondly, the alcohols formed are not nucleophilic enough in comparison to the deprotonated amino alcohol in order to react with the alkylating or benzylating agent used.

In a particular embodiment, a further solvent whose boiling point is between the water which forms and the other solvent may be used. This reaction allows the better removal of the water. The further solvents used are preferably alcohols, aliphatic and aromatic ethers and ketones, both cyclic and acyclic; particular preference is given to those having a number of carbon atoms between 2 and 10, in particular C2-C10-alcohols, C2-C10-ethers and C2-C10-ketones.

In the inventive reaction, the procedure is preferably to initially charge the substrate and the base in the solvent at temperatures of 20-200° C., preferably 100-150° C., more preferably at the boiling point of the solvent used. Low-boiling solvents, especially the water formed and any second solvent used, can subsequently be removed by distillation. Thereafter, the alkylating agent or benzylating agent is added at temperatures of 20-200° C., preferably 50-150° C., more preferably at the boiling point of the solvent used. The pressure at which the reaction is carried out is not critical per se. For practical reasons, the reaction is preferably carried out at 500-5000 hPa, more preferably at standard pressure.

In the context of the invention, the term diastereomerically enriched is understood to mean the fraction of one diastereomer in a mixture with other diastereomeric isomers in a region of >50% and <100%.

The chiral structures shown relate to all possible diastereomers and enantiomers (R,S), and also mixtures thereof and the racemate.

By virtue of generating the amino alkoxide salts by means of alkali metal alkoxides in a process for preparing cyclic O-alkylated or O-benzylated amino alcohols by reacting cyclic N-unsubstituted or N-monosubstituted amino alkoxide salts with alkyl halides or benzyl halides in solvents, the solution to the stated objective is arrived at in a manner which is entirely surprising but very simple and particularly advantageous in accordance with the invention.

While it originally had to be assumed that very strong bases (for example hydrides) should be employed for the reaction, it was found in the present invention that alkali metal alkoxides, preferably in the corresponding alcohol, are capable of this. This leads to the ability to dispense with the use of the costly strong bases, some of which are dangerous. It has also been found that, surprisingly, the O-alkylation can be carried out selectively with alkoxides as bases on cyclic amino alcohols, which generally have a lesser tendency to undesired side reactions.

WORKING EXAMPLES

Example 1

340 kg of an approx. 35% trans-2-aminocyclohexanol solution in xylene isomer mixture and a further 400 kg of xylene isomer mixture are heated to reflux in a tank. 240 kg of a 30% methanolic sodium methoxide solution are metered into this solution over three hours, in the course of which the tank temperature should not rise above 140° C. In the course of this, methanol is distilled off. After the addition has ended, methanol is distilled off until the distillation temperature is at 140-145° C. At a tank temperature of 135° C., 153 kg of benzyl chloride are then metered in over six hours. After the addition has ended, the mixture is left to stir at 140° C. for a further two hours. Aqueous workup affords 172 kg of crude effluent (56% product, GC). The product was isolated by means of a fractional distillation at a pressure of 10 hPa and a temperature of about 160° C. 109 kg of the desired product (overall yield of 51%) with a purity of >99.7% (GC) were obtained.

Example 2

35.9 g of potassium tert-butoxide are initially charged in 100 ml of tetrahydrofuran and heated to 60° C. 30.3 g of trans-2-aminocyclohexanol dissolved in 100 ml of tetrahydrofuran are added dropwise to this solution over 20 minutes. The mixture is then left to stir at 60° C. for 30 minutes and 32.9 g of benzyl chloride are subsequently added within a half hour such that the temperature remains at 60° C. After the addition has ended, the solution is stirred at 60° C. for two hours and then admixed with 60 ml of water. Extraction affords the desired O-benzylated product in a yield of 86% (GC area %).

Example 3

30.3 g of trans-2-aminopentanol and 35.9 g of potassium tert-butoxide are initially charged in 100 ml of tetrahydrofuran and heated to 60° C. 32.9 g of benzyl chloride are added dropwise to this mixture over one hour. After the addition has ended, the reaction mixture is left to stir at 60° C. for three hours and then worked up under aqueous conditions. 2-Benzyloxycyclopentylamine is obtained in 81% (GC area %).

What is claimed is:

1. A process for preparing O-benzylated amino alcohols of the formula (I):

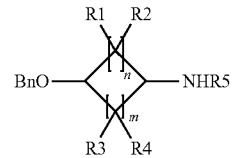

the process comprising:
reacting N-monosubstituted amino alkoxide salts with substituted or unsubstitued benzyl halides, the N-monosubstituted amino alkoxide salts being formed by deprotonation with an alkoxide,
wherein
n=0 and m=3 or 4, and
R3, and R4 are H, R5 is a substituted and unsubstituted $(C_1-C_8)$-alkyl, $(C_3-C_8)$-cycloalkyl, $(C_1-C_8)$-alkyl-$(C_3-C_8)$-cycloalkyl, $(C_3-C_8)$-cycloalkyl-$((C_1-C_8)$-alkyl)1-3, $(C_2-C_8)$-alkenyl, $(C_2-C_8)$-alkynyl, $(C_6-C_{18})$-aryl, $(C_7-C_{19})$-aralkyl radical, $(C_6-C_{18})$-aryl-$((C_1-C_8)$-alkyl)1-3, and Bn being a substituted or unsubstituted benzyl, and
wherein the reaction is carried out in xylene,
with the proviso that the process is carried out in the absence of alkali metal hydrides.

2. The process according to claim 1, wherein the amino alkoxide salts are obtained by potassium tert-butoxide.

* * * * *